(12) United States Patent
Campbell et al.

(10) Patent No.: US 10,481,107 B2
(45) Date of Patent: Nov. 19, 2019

(54) SCANNING INSTRUMENT

(71) Applicant: JOHNSON MATTHEY PUBLIC LIMITED COMPANY, London (GB)

(72) Inventors: James Campbell, Hertfordshire (GB); Emanuele Ronchi, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 543 days.

(21) Appl. No.: 15/106,977

(22) PCT Filed: Dec. 18, 2014

(86) PCT No.: PCT/GB2014/053765
§ 371 (c)(1),
(2) Date: Jun. 21, 2016

(87) PCT Pub. No.: WO2015/097449
PCT Pub. Date: Jul. 2, 2015

(65) Prior Publication Data
US 2017/0030844 A1 Feb. 2, 2017

(30) Foreign Application Priority Data
Dec. 23, 2013 (GB) .................................. 1322944.8

(51) Int. Cl.
*G01N 23/18* (2018.01)
(52) U.S. Cl.
CPC ....... *G01N 23/18* (2013.01); *G01N 2223/628* (2013.01); *G01N 2223/646* (2013.01)
(58) Field of Classification Search
CPC ............. G01N 23/18; G01N 2223/628; G01N 2223/419
(Continued)

(56) References Cited
U.S. PATENT DOCUMENTS
3,673,407 A 6/1972 Wiswell, Jr.
3,735,129 A 5/1973 Montgomery et al.
(Continued)

FOREIGN PATENT DOCUMENTS
GB 2 200 206 A 7/1988
GB 2492486 A 1/2013
(Continued)

OTHER PUBLICATIONS
International Search Report, dated Apr. 8, 2015, from corresponding PCT Application.
(Continued)

*Primary Examiner* — David P Porta
*Assistant Examiner* — Carolyn Fin
(74) *Attorney, Agent, or Firm* — BakerHostetler

(57) ABSTRACT

A scanning apparatus for measuring the attenuation of radiation passing from a radiation source along a radiation path to a radiation detector includes a source of radiation; at least one radiation detector capable of detecting radiation emitted by the source a data processor associated with the at least one radiation detector for calculating a property of material present in a linear radiation path between the source and the at least one detector; and a spacer arranged between the source and the at least one detector. The spacer defines a space which is capable of excluding water and having an average density which is less than 1 $gcm^{-3}$. The provision of a spacer in the radiation path enables more radiation to be passed along the radiation path because water can be replaced with a material which is less attenuating to radiation.

14 Claims, 2 Drawing Sheets

(58) Field of Classification Search
USPC .................................................. 250/358.1
See application file for complete search history.

(56) References Cited

U.S. PATENT DOCUMENTS

| | | | |
|---|---|---|---|
| 3,891,845 A | | 6/1975 | English |
| 4,955,012 A | * | 9/1990 | Bledsoe ................. G01V 1/208 367/149 |
| 7,209,540 B2 | * | 4/2007 | Muhanna ............. G01V 5/0016 378/57 |
| 8,938,046 B2 | * | 1/2015 | Hunter ................... G01N 23/04 378/181 |

FOREIGN PATENT DOCUMENTS

| | | | |
|---|---|---|---|
| GB | 2496736 A | | 5/2013 |
| JP | S53-103791 A | | 9/1978 |
| JP | S61-271443 A | | 12/1986 |
| JP | H1-224652 A | | 9/1989 |
| WO | 2013/064838 A1 | | 5/2013 |

OTHER PUBLICATIONS

United Kingdom Search Report, dated Jun. 11, 2014, from corresponding GB Application.
United Kingdom Search Report, dated Jun. 11, 2015, from corresponding GB Application.

* cited by examiner

SCANNING INSTRUMENT

The present invention concerns apparatus for use in water, for example scanning or measurement instruments for use in sub-sea environments.

Scanning instruments may be used in a variety of locations which involve immersion in water, for example for scanning pipelines and other apparatus used sub-sea in the oil and gas production industry. Scanning methods for determining structural characteristics or composition of plant and equipment may involve the measurement of radiation, for example gamma radiation, which has passed through the part which is scanned. When the measurement is carried out in water, the presence of water between the source of the radiation and the detector may affect the measurement. As an example, such measurements may derive the measured characteristics from the measurement of density which is itself measured by determining the attenuation of radiation as is passes through the scanned part. When the radiation passes through water in addition to the scanned part, the radiation is attenuated by the water so that the attenuation of radiation due to the scanned part is more difficult to determine with precision. Furthermore, since the amount of radiation passing through a scanned part to reach a radiation detector may be small if the part is dense, the measurement of such radiation becomes difficult and subject to error. Therefore it is advantageous to reduce the amount of water through which radiation must pass in such scanning operations.

A particular method of scanning pipelines, which may be underwater, was described in WO2013/064838. In that method a source of gamma radiation and an array of radiation detectors is rotated around a part to be scanned, such as a pipeline. The detector array is precisely arranged relative to the source so that the scanning can be carried out at high resolution. Such precision apparatus is large and expensive to build. It is therefore advantageous to be able to use it for scanning a variety of parts, for example pipelines of different dimensions. When the scanning apparatus is designed to accommodate large-diameter pipelines it may also be used to scan smaller diameter objects. However when the apparatus is used in water to scan pipelines which are smaller than the maximum diameter for which the apparatus is designed, a significant portion of the radiation path between the source and a detector may pass through water, causing attenuation of the radiation and consequently a reduction in the radiation which is measured by a detector. When the amount of radiation detected is small it is necessary to collect radiation over a longer time period in order to obtain a high resolution scanning result, resulting in more time-consuming and expensive scanning operations for a given amount of pipeline. When the amount of radiation detected is small, systematic errors on the measurement can dominate, making measurement extremely difficult. It is an object of the invention to provide an improved apparatus and method for scanning.

According to the invention, a scanning apparatus for measuring the attenuation of radiation passing from a radiation source along a radiation path to a radiation detector comprises:
 a) a source of radiation;
 b) at least one radiation detector capable of detecting radiation emitted by said source;
 c) a data processor associated with said at least one radiation detector for calculating a property of material present in a linear radiation path between said source and said at least one detector;

characterised in that said apparatus further comprises a spacer arranged between said source and said at least one detector, said spacer defining a space which is capable of excluding water and having an average density which is less than 1 $gcm^{-3}$.

The spacer has an average density less than 1 $gcm^{-3}$. The spacer may have an average density <0.75, especially <0.5 $gcm^{-3}$. The spacer may comprise a shell enclosing a vacuum or a gas. In such an embodiment the gas may comprise air or an inert gas such as nitrogen or helium. A proportion of the volume of the spacer may be filled by a solid foamed material. Suitable solid foamed materials comprise a solid material forming pores which are filled with a gas or a vacuum. The solid material typically comprises a polymer. The polymer may comprise a synthetic polymer, including, for example, a polyurethane. The foamed material may be rigid or flexible, i.e. elastomeric. The foamed material may be enclosed within a shell which is impervious to water. The spacer may be formed from a commercial buoyancy material. Commercially available buoyancy material of the type which is designed and sold for use with an ROV may be particularly suitable for some applications. Various types of such buoyancy material are offered for sale by a variety of companies.

The shell may be rigid or flexible. The shell may be shaped to be adapted or adaptable to the shape of a part of the scanning apparatus. The shell is formed from a material which is impervious to the ingress of water into the volume occupied by the spacer. Suitable materials may include metals, for example steel or aluminium, and polymeric materials, for example polyurethane, polyethylene or a polymer composite. The use of a metallic material to form a part of the spacer may be disadvantageous when the radiation emitted by the source and detected by a detector is attenuated by metal. When the scanning apparatus operates by the detection of gamma radiation by the at least one detector, it is preferred that the shell, if present, is formed, at least partly, from a polymeric material. The spacer may comprise a part which is formed from a different material from the shell or the foamed material. For example, a spacer which is formed from a polymeric shell material may include at least one portion which is formed from a metal. In such a case it is preferred that the metallic portion is deployed out of the linear radiation path.

The spacer is preferably capable of maintaining its shape when subjected to hydrostatic compression, which is experienced when the scanning apparatus is deployed in water. When the scanning apparatus is intended to be used at significant depths, for example >1 m, a rigid shell which is capable of withstanding hydrostatic pressure without deforming to a significant extent may be preferred. Therefore a rigid polymeric or metal shell may be preferred for such applications.

More than one spacer may be associated with the scanning apparatus. A spacer may be provided to be positioned between the radiation source and the object to be scanned. A spacer may be provided to be positioned between a radiation detector and the object to be scanned. When the scanning apparatus is used for scanning a pipeline, different spacers may be provided to fit between the radiation source or the radiation detector and pipes of different dimensions. A spacer may be mounted to the scanning apparatus in such a way that it is movable with a part of the scanning apparatus. A spacer may be mounted in a fixed relationship with respect to the source. A spacer may be mounted in a fixed relationship with respect to the at least one radiation detector.

A spacer may be formed from a plurality of spacer portions which are adapted to engage each other to form a combined spacer which fills a greater volume than any of the separate spacer portions. Pipelines used in industry may be of a relatively small number of standard sizes. Spacers and spacer portions may be fabricated to accommodate different standard sizes of pipe within the internal diameter of the spacer and having an outer diameter to fit within the scanning apparatus. The spacer potions may be fixed to each other and to the scanning apparatus by means of fixings which can be operated to attach and detach the spacers and/or spacer portions. The fixings are located out of the radiation path, so far as possible, in order to avoid attenuation of radiation by the material of the fixings.

The spacer may contribute to the buoyancy and trim of the scanning apparatus in water. The spacer may be designed to be of such a density and shape as to facilitate the positioning, orientation and/or manoeuvrability of the scanning apparatus underwater. The spacer may comprise removable weights in order to adjust the trim of the scanning apparatus.

The spacer may be fixed to the object to be scanned. In such a case, the outer part of the spacer is adapted to fit within the scanning apparatus. The inner part of the spacer is adapted to fit to the object to be scanned. The spacer may be fixed to the object to be scanned, for example by means of one or more clamps or cables. The spacer may be fitted to the object before the scanning operation has begun. It is preferred that the spacer may be removed from the object or moved to a different part of the object when the scanning operation is completed. A method of scanning an object according to an embodiment of the invention may therefore comprise the steps of attaching to the object a spacer defining a space which is capable of excluding water and having an average density which is less than 1 gcm$^{-3}$ then placing a scanning apparatus adjacent said spacer and carrying out a scanning operation using said scanning apparatus.

The scanning apparatus may comprise a pipe-scanning apparatus of the type described in WO2013/064838. Alternatively the scanning apparatus may comprise a different apparatus in which radiation is used to estimate the density along a path through an object or structure.

In a typical scanning apparatus, the source may be housed in a source unit comprising a source of penetrating radiation, a source-holder and a collimator. The collimator and source-holder may be combined. The collimator is formed of a material which is highly attenuating to the radiation emitted by the source and is normally formed of a heavy alloy material of the type known and commonly used for shielding radiation of the appropriate energy and type. The collimator is located and adapted to limit the radiation emitted by the source unit to a predetermined beam shape and direction. Preferably the radiation beam is shaped by the collimator to form a fan cone, frusto-cone, or sector in each case having the source as origin. A preferred beam shape is a cylindrical sector, i.e. a sector having a thickness rather than being planar. Preferably the beam is collimated to provide a beam area at the location of the detector(s) which has the same general shape and area as the combined detecting surface(s) of the array of detectors. The source unit may be mounted on a support.

The radiation source is selected by the transparency to the radiation of the material(s) to be measured, e.g. a vessel and/or its contents (i.e. the attenuation coefficient of the medium) and the availability of suitable sources and detectors. For scanning large solid structures such as process vessels and pipelines, suitable sources of gamma include $^{80}$Co and $^{137}$Cs, $^{133}$Ba, $^{241}$Am, $^{24}$Na and $^{182}$Ta, however any gamma-emitting isotope of sufficient penetrating power could be used, and many such are already routinely used in density gauges, such as those used as level measurement devices. Usually, the half-life of the radioisotope used will be at least 2, and desirably at least 10, years. The half-lives of the radioisotopes mentioned above are: $^{137}$Cs gamma about 30 years, $^{133}$Ba about 10 years and $^{241}$Am about 430 years. Suitable sources generally emit radiation at energies between about 40 and 1500 keV.

The source unit may include one or more than one source. The scanning method may utilise more than one source unit if required.

The scanning apparatus may comprise an array of radiation detectors. For example the scanning unit may comprise an array of at least 10 detectors. The detector, or each of the detectors, may comprise a scintillator, normally supported in a suitable position so that a surface thereof, which may be referred to as the detecting surface, intersects a path of radiation emitted by the source at a particular distance from and a particular angle to the radiation source. The detector or each detector of a detector array may be housed within a collimator which reduces the detection of radiation impinging on the detector from an angle outside the angle of a linear radiation path from the source. The collimator comprises a material which is impermeable to the radiation emitted by the source. The collimator may cover a part of the detecting surface of the detector to delimit the portion of the detecting surface on which radiation may impinge.

When the detector unit comprises more than one detector, deployed in the form of an array of detectors, a preferred embodiment of the invention comprises a block of shielding material (a "detector block") having openings extending inwardly from a surface of the block, each opening containing a detector, the detecting surface being accessible to radiation from outside the block. A portion of the detecting surface may be covered by shielding material for the purposes of delimiting the area of the detecting surface or for mechanically retaining the detector within the opening. The non-detecting surfaces of the detector may optionally be enclosed partially or wholly within the opening and covered by the shielding material. The detector block includes means by which the collecting surface of the scintillator(s) may be brought into contact with a photodetector or a light transmitter. Such means may take the form of an open passage through which the scintillator extends so that the collecting surface is accessible to the photodetector or light transmitter.

When the detector comprises a scintillation material, such as a scintillation crystal or a polymeric scintillator, a photodetector is provided which is optically coupled to the scintillator in order to detect and measure light generated by the scintillator in response to photons of radiation from the source. The photodetector may be a photodiode, photomultiplier tube (PMT), a silicon photomultiplier or other suitable light detecting device. The photodetector generates an electrical signal in response to light entering it through an optical window. The wavelengths detected by the photodetector should be matched as far as possible to the wavelengths generated by the scintillator to maximise the detection efficiency. Normally a photodetector is provided for each scintillator so that the amount of radiation detected by each scintillator can be measured independently of the other scintillators.

Each detecting surface preferably forms a tangent to an arc of a circle having a radiation source as its origin. In one embodiment, each detector surface forms a tangent to the surface of a part of a sphere having the radiation source as its origin.

Other forms of radiation detector may be employed in a scanning apparatus of the invention. For example, Geiger-Müller tubes or other detectors may be used.

The apparatus further comprises a signal/data processor for operating on the electrical signal from the detectors in the detector unit(s) and a controller to control the operation of the apparatus. Signals representative of the counts of photons detected by the scintillators are processed by the data processor. The signal may be subjected to smoothing or stabilisation algorithms, averaged or otherwise operated on according to standard practices. A data processor may perform calculations based on the signal from the radiation detector or from a signal processor if present. The data processor may output information concerning the amount of radiation measured over a time interval, or it may further calculate derived properties of the scanned structure, usually in the form of a bulk density or a change in bulk density between radiation paths through the structure. The scanning method is carried out at a plurality of radially offset positions around the structure so that density data may be acquired at a variety of angles through the structure and a tomography algorithm may be used to provide information about the changes in density at different paths through the structure. In a preferred form the data from the detectors is operated on by the data processing unit using tomography algorithms in order to produce a graphical representation of the density or composition of the structure along different paths. The data processor may contain a calibration or information concerning the radiation source. The data processor output is may be connected a display or a (optionally wireless) transmission means so that a signal can be sent from the apparatus to a remote location. Alternatively a signal comprising data from the radiation detector itself may be sent, for processing at a remote location. A power supply is provided to power the photodetectors, data processor and control electronics and also to power motors for moving the apparatus. Movement of the scanning apparatus, for example to open and close the apparatus and to rotate the source and detector, may be accomplished by means of electrically or hydraulically powered motors or actuators In use in one form of the scanning method of the invention, the apparatus is deployed so that the source unit and detector units are positioned in relation to the structure to be scanned so that one or more radiation paths from the source to detectors in the detector unit pass through the desired portion of the structure. The amount of radiation, in the form of counts, is measured by the detector in each detector unit deployed in the apparatus. The scanning method is carried out at a plurality of radially offset positions around the structure so that density data may be acquired at a variety of angles through the structure. The apparatus may then be moved to a different location or orientation with respect to the structure and the measurement is repeated. In this way a record of the attenuation to radiation through each radiation path through the structure may be gathered and used to calculate the location of changes or to build a representation of the structure and its contents. Information such as changes in density which may highlight flaws or other features within the structure can be obtained from the data gathered from the detectors using data analysis tools known for use in tomography methods.

An example incorporating several optional features of the invention will be described with reference to the appended drawings.

Figure 1:
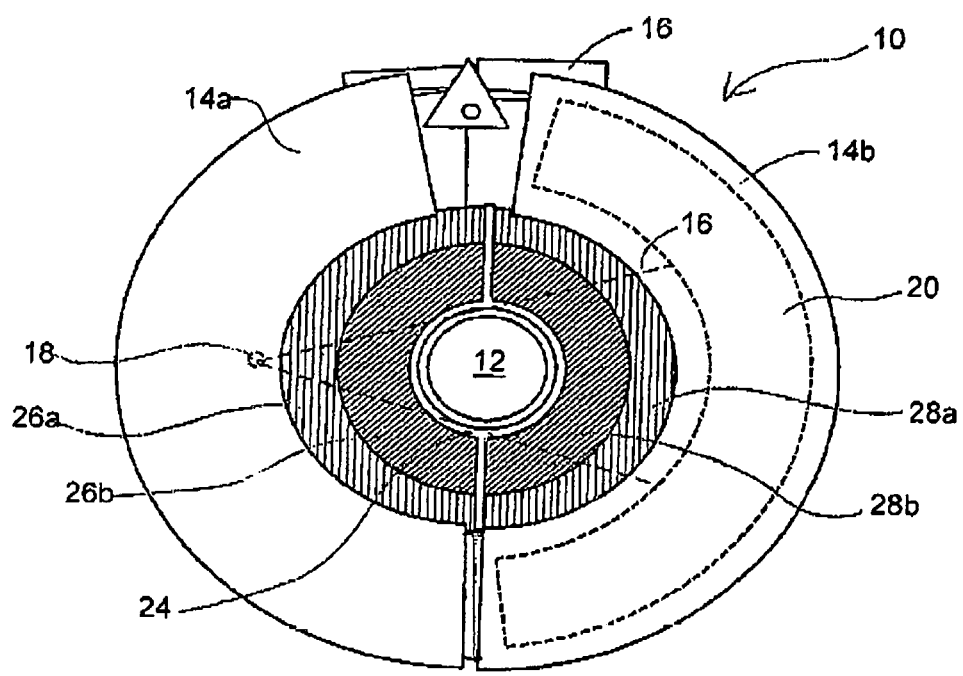
FIG. 1 is a schematic view of a section of a pipe enclosed within a scanning apparatus of the invention.

FIG. 1 shows a pipe scanning apparatus 10 surrounding a pipeline 12 (shown in section). The scanning apparatus comprises a pair of hinged housings 14a & 14b which open and close by means of hydraulic apparatus 16. When the housings are open the apparatus may be moved around the pipe to be scanned and then closed around it. A source of gamma radiation 18 is located within housing 14a together with collimation and shielding to emit a collimated cone of radiation towards the detector array. An arcuate array of radiation detectors 20 is located in housing 14b. The source and the detector array are fixed in relation to each other but are rotatable around the pipeline. Each detector of the detector array detects radiation from the source which has passed along a portion of the cone-shaped path between the source and the detector. A number of radiation paths may be defined, each radiation path being between the source and each detector in the detector array. When a radiation path intersects the pipe, as shown, for example, by the dashed line 22, the radiation is attenuated by the material of the pipe wall so that the radiation detected by a radiation detector in that path is less than the radiation detected by a detector located in a path which intersects less of the pipe material. In that way, information can be collected about the density of material along each radiation path and, by means of the rotation of the source and detector array and a tomography algorithm, an image of the pipeline wall thickness may be assembled.

Figure 2:
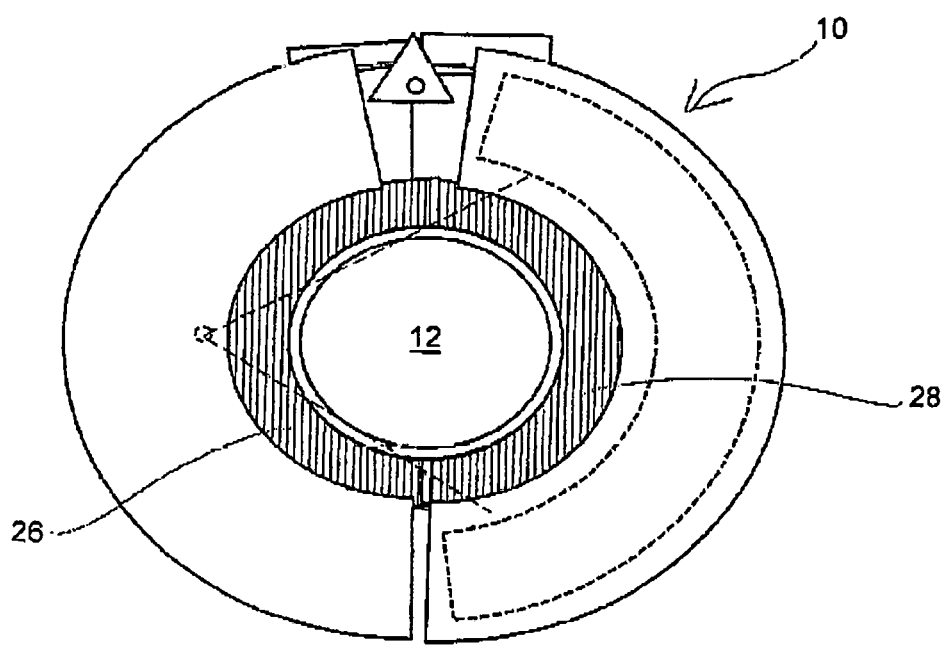
FIG. 2 is a similar view to that of FIG. 1, showing a different arrangement of the scanning apparatus.

The maximum diameter of pipeline which can be scanned using the scanning apparatus 10 is limited by the internal diameter of the housings 14a/b. When pipe 12 is of significantly smaller diameter than the internal diameter of the housings, the gap 24 between the source and the pipeline and the detector array and the pipeline may be relatively large. When the pipeline is located underwater, the gap 24 is filled by water which attenuates radiation from the source so that fewer radiation counts are detected by the detectors along each path, affecting the resolution of the instrument. To alleviate this problem, a part of gap 24 is filled by spacers 26 and 28 which are formed from a rigid-skinned foam buoyancy material. The buoyancy foam material has a density of about 0.5 $gcm^{-3}$, which is significantly less than that of the water which it replaces in the gap. If 15 cm of the length of the radiation path which would pass through water is replaced by a material having a density of 0.4 $gcm^{-3}$, then the counts detected by the radiation detector should be doubled. The spacer material is therefore less attenuating to radiation than water. The result is that more radiation is detected by each detector. In the embodiment shown, the spacer 26 is formed from two parts 26a and 26b which together fill a greater part of the gap between pipe 12 and source 18. Likewise, spacer 28 is formed from spacer portion 28a and spacer portion 28b. In the drawings, gaps between the spacer portions and between the spacer and pipe may be exaggerated for clarity. If a larger pipe than pipe 12 is to be scanned by the apparatus shown, the pipe may be accommodated by removing spacer portions 26b and 28b. This arrangement is shown in FIG. 2 in which the spacers are shown as 26 and 28. When still larger pipes are to be scanned the spacers may be completely removed from the apparatus. In practice, pipelines used in industry may be of a relatively small number of standard sizes. Spacers and spacer portions may be fabricated to accommodate various of the standard sizes. The spacer potions may be fixed to each other and to the scanning apparatus by means of fixings which can be operated to attach and detach the spacers and/or spacer portions. The fixings are located out of the radiation path so far as possible in order to avoid attenuation of radiation by the material of the fixings.

Figure 3:
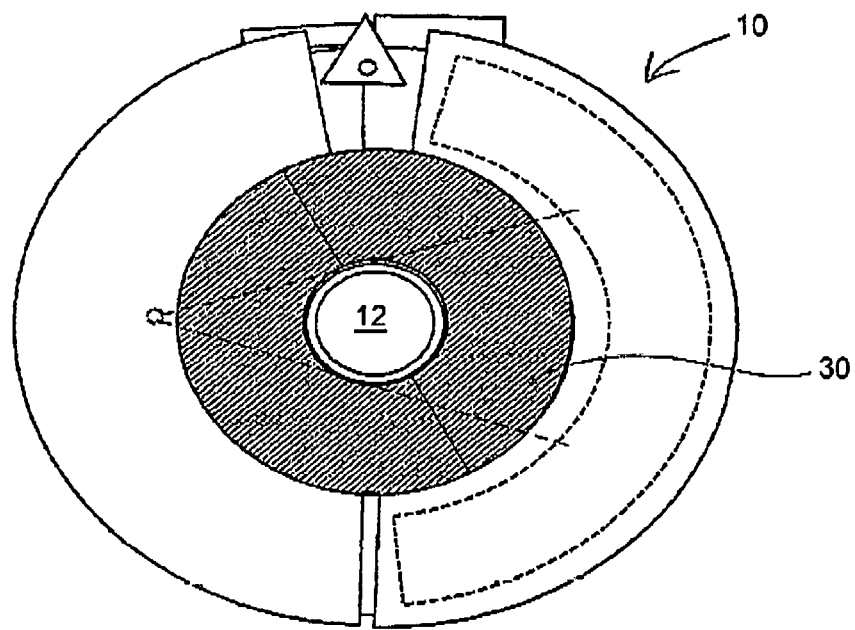
FIG. 3 is a similar view to that of FIG. 1, showing a different arrangement of the scanning apparatus.
Figure 4:
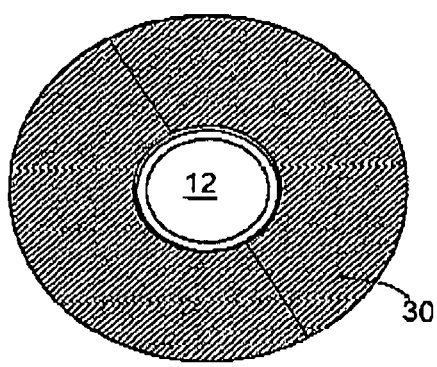
FIG. 4 shows, in section, a spacer fixed to a pipeline.
Figure 5:
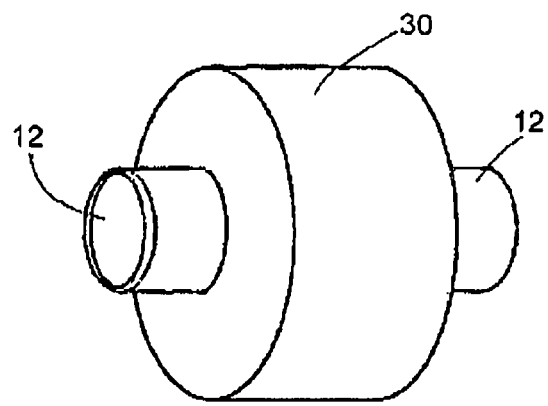
FIG. 5 shows, in perspective, a schematic view of a spacer fixed to a pipeline.

FIG. 3 shows a similar arrangement, except that the spacer 30 comprises one spacer which is of a size and shape to fit pipe 12. The spacer may be fitted to the pipe instead of to the scanning instrument. It may be convenient to fit a spacer to a pipe before it is scanned. FIGS. 4 and 5 show a pipeline 12 fitted with a spacer 30 made of a buoyancy foam. The outside diameter of the spacer is selected to fit into the scanning apparatus. The scanning apparatus is placed over the spacer 30 before the scanning operation is started. The spacer 30 may be removed or moved to a different portion of pipeline when the scanning operation is completed.

The invention claimed is:

1. A sub-sea pipeline scanning apparatus for measuring the attenuation of gamma radiation passing from a source of gamma radiation along a radiation path through a sub-sea pipeline to a radiation detector comprising:
  a) the source of gamma radiation;
  b) the radiation detector, which is capable of detecting gamma radiation emitted by said source and passed through the sub-sea pipeline,
  wherein the sub-sea pipeline scanning apparatus is configured to rotate the source and the at least one radiation detector around the sub-sea pipeline while maintaining the source and the at least one radiation detector in a fixed relationship to each other;
  c) a data processor associated with said at radiation detector configured to calculate a property of a material present in a linear radiation path between said source and said radiation detector;
  wherein said sub-sea pipeline scanning apparatus further comprises:
  a first spacer mounted in a fixed relationship with respect to the source and positioned, between the source and the sub-sea pipeline to be scanned; and
  a second spacer mounted in a fixed relationship with respect to the radiation detector and positioned, between the radiation detector and the sub-sea pipeline;
  wherein said first and second spacers are rotatable around the sub-sea pipeline with the source and the radiation detector, and said first and second spacers each define a space which is capable of excluding water and have an average density which is less than 1 $gcm^{-3}$.

2. The scanning apparatus according to claim 1, wherein the first and/or second spacer has an average density <0.75 $gcm^{-3}$.

3. The scanning apparatus according to claim 2, wherein the first and/or second spacer comprises a shell enclosing a vacuum or a gas.

4. The scanning apparatus according to claim 2, wherein a proportion of the volume of the first and/or second spacer is filled by a solid foamed material.

5. The scanning apparatus according to claim 2, wherein the first and/or second spacer comprises a shell which is impervious to water.

6. The scanning apparatus according to claim 2, further comprising removable weights for adjusting a trim of the scanning apparatus when underwater.

7. The scanning apparatus according to claim 2, wherein each of the first and second spacers are formed from a plurality of spacer portions which are adapted to engage each other to form the first and second spacers, wherein the first and second spacers each fill a greater volume than any of the separate spacer portions.

8. The scanning apparatus according to claim 1, wherein the first and/or second spacer comprises a shell enclosing a vacuum or a gas.

9. The scanning apparatus according to claim 1, wherein a proportion of the volume of the first and/or second spacer is filled by a solid foamed material.

10. The scanning apparatus according to claim 1, wherein the first and/or second spacer comprises a shell which is impervious to water.

11. The scanning apparatus according to claim 10, wherein said shell is rigid or flexible.

12. The scanning apparatus according to claim 1, wherein the first and/or second spacer comprises a buoyancy material.

13. The scanning apparatus according to claim 1, further comprising removable weights for adjusting a trim of the scanning apparatus when underwater.

14. The scanning apparatus according to claim 1, wherein each of the first and second spacers are formed from a plurality of spacer portions which are adapted to engage each other to form the first and/or second spacer, wherein the first and second spacers each fill a greater volume than any of the separate spacer portions.

* * * * *